United States Patent [19]

Fruth et al.

[11] Patent Number: 5,231,228
[45] Date of Patent: Jul. 27, 1993

[54] PROCESS FOR THE PREPARATION OF SATURATED PRIMARY FATTY AMINES BY HYDROGENATION OF THE CORRESPONDING UNSATURATED PRIMARY FATTY AMINES

[75] Inventors: Anton Fruth, Garching; Julius Strauss, Altötting; Herbert Stühler, Burgkirchen, all of Fed. Rep. of Germany

[73] Assignee: Hoechst Aktiengesellschaft, Frankfurt am Main, Fed. Rep. of Germany

[ * ] Notice: The portion of the term of this patent subsequent to 12/12/08, has been disclaimed.

[21] Appl. No.: 806,042

[22] Filed: Dec. 12, 1991

[30] Foreign Application Priority Data

Dec. 14, 1990 [DE] Fed. Rep. of Germany ....... 4039935

[51] Int. Cl.$^5$ ............................................ C07C 209/70
[52] U.S. Cl. .................................................... 564/463
[58] Field of Search ......................................... 564/463

[56] References Cited

U.S. PATENT DOCUMENTS

| | | | |
|---|---|---|---|
| 3,293,298 | 12/1966 | Szabo | 260/583 |
| 4,139,560 | 2/1979 | Reinehr et al. | 564/463 |
| 4,248,801 | 2/1981 | Tomidokaro et al. | 564/463 |

Primary Examiner—Allen J. Robinson
Assistant Examiner—Scott C. Rand
Attorney, Agent, or Firm—Connolly and Hutz

[57] ABSTRACT

Process for the preparation of saturated primary fatty amines by hydrogenation of the corresponding unsaturated primary fatty amines In the novel process, the hydrogenation of the double bonds in an unsaturated primary fatty amine is achieved by reaction of the unsaturated primary fatty amine with hydrogen at a temperature of 80° to 160° C. and a pressure of 1 to 40 bar in the liquid phase and in the presence of 0.1 to 10% by weight of a nickel catalyst or cobalt catalyst. If the fatty amine to be hydrogenated contains ammonia, the latter is substantially removed before the hydrogenation process.

12 Claims, No Drawings

PROCESS FOR THE PREPARATION OF SATURATED PRIMARY FATTY AMINES BY HYDROGENATION OF THE CORRESPONDING UNSATURATED PRIMARY FATTY AMINES

The invention relates to a process for the preparation of saturated primary fatty amines by hydrogenation of unsaturated primary fatty amines in the liquid phase in the presence of nickel catalysts or cobalt catalysts.

The preparation of saturated primary fatty amines is generally accomplished in the prior art by hydrogenation of the corresponding saturated fatty acid nitriles. Thus in U.S. Pat. No. 3,293,298, a process is described for the preparation of saturated primary fatty amines, such as laurylamine, stearylamine and sebacylamine, in which a corresponding alkylnitrile is hydrogenated in the presence of a nickel catalyst and in the presence of ammonia at a temperature of 120° to 150° C. and at a hydrogen pressure of 5 to 25 bar. The use of a more or less large quantity of ammonia is held to be necessary to suppress the formation of the secondary and tertiary amine by-products, and to achieve a high yield of saturated primary fatty amine.

In the case of the hydrogenation of unsaturated fatty acid nitriles to saturated primary fatty amines using nickel catalysts or cobalt catalysts, the opinion generally prevails that in addition to the use of ammonia, a relatively high pressure and/or a high temperature must also be employed, so that not only is the nitrile group hydrogenated to the primary amino group, but the olefinic double bonds are also hydrogenated. On the basis of the prior art, it appears therefore that the hydrogenation of olefinic double bonds in the unsaturated primary fatty amine requires high pressures and/or high temperatures, and also the presence of a relatively large amount of ammonia.

It is accordingly the object of the invention to provide a process for the hydrogenation of olefinic double bonds in an unsaturated primary fatty amine, by means of which this hydrogenation and thus the preparation of saturated primary fatty amines may be achieved simply and in high yield.

The process according to the invention for the preparation of saturated primary fatty amines by hydrogenation of unsaturated primary fatty amines in the liquid phase in the presence of nickel catalysts or cobalt catalysts comprises reacting the unsaturated primary fatty amine with hydrogen in the presence of 0.1 to 10% by weight of said catalyst, preferably 0.5 to 5% by weight of said catalyst, relative to the fatty amine, at a temperature of 80° to 160° C., preferably 100° to 140° C., and a pressure of 1 to 40 bar, preferably 1 to 25 bar.

It is surprising that saturated primary fatty amines are obtained in a high yield by means of the process according to the invention, since the opinion prevails that primary fatty amines, in the presence of metals, such as nickel, cobalt, palladium and the like, eliminate ammonia even at a temperature of about 100° C., and that this can be prevented only by use of a more or less high partial pressure of ammonia.

The starting material for the process according to the invention is unsaturated fatty amines having 8 to 22 carbon atoms, preferably 12 to 18 carbon atoms, or their mixtures or mixtures of these fatty amines and up to 90% by weight, preferably up to 60% by weight, of saturated primary fatty amines of the chain length mentioned, the percentages by weight being relative to the sum of the weights of the saturated and unsaturated primary fatty amines. The fatty amines used as starting material are thus unsaturated primary fatty amines having 8 to 22 carbon atoms, preferably 12 to 18 carbon atoms, and preferably having 1 to 3 (conjugated or preferably isolated) double bonds or their mixtures. Just as suitable are also mixtures of unsaturated and saturated primary fatty amines, preferably those obtained on hydrogenation of fatty acid nitriles, which are themselves prepared from fatty acids of naturally occurring fats and oils, for example the mixtures of primary fatty amines obtained on hydrogenation of the nitriles of tallow fatty acid, coconut fatty acid, palm kernel fatty acid, fish fatty acid, cottonseed oil fatty acid, rapeseed oil acid, rice oil acid, sunflowerseed oil acid and soybean oil acid. These mixtures can contain, in addition to the unsaturated primary fatty amines, up to 90% by weight, preferably up to 60% by weight, of saturated primary fatty amines having 8 to 22 carbon atoms, preferably having 12 to 18 carbon atoms. The process according to the invention is thus applicable to unsaturated primary fatty amines having 8 to 22 carbon atoms, preferably 12 to 18 carbon atoms, which contain 0 to 90% by weight, preferably 0 to 60% by weight, of saturated primary fatty amines having 8 to 22 carbon atoms, preferably 12 to 18 carbon atoms. The primary fatty amines in question have iodine numbers from about 10 to 100. Thus the tallow fatty amines mentioned normally have an iodine number of 30 to 60 (as is known, the iodine number indicates the consumption in g of iodine per 100 g of substance).

The process according to the invention, on use of the primary fatty amines mentioned, accordingly gives a reaction product comprising saturated primary fatty amines having 8 to 22 carbon atoms, preferably 12 to 18 carbon atoms, in the alkyl chain (the alkyl chains may be identical or different).

The process according to the invention is carried out by introducing the unsaturated primary fatty amine or amines or the mixture of unsaturated and saturated primary amines into an autoclave equipped with a heating-/cooling jacket and a highly effective stirrer. A reactor can also be used in which the contents are continuously circulated by pump. A heat exchanger having heating and cooling ability and an injector which continuously draws in gas from the reactor are installed in the circulation line. The reaction vessels have in addition devices for introduction and removal of gases, for filling and emptying, and for monitoring and regulation of pressure and temperature. As far as is practicable, the fatty amine used is introduced in the molten state. The reaction vessel is furthermore charged with the catalyst intended for the hydrogenation of the amine. Suitable catalysts are nickel and cobalt catalysts which can be doped with traces of other metals, examples of which are calcium, barium, iron, manganese and molybdenum, and which may be used in the form of supported catalysts, in particular as powders, or in the form of Raney catalysts. Examples of suitable materials for supported catalysts are aluminum oxide, silica gel, kieselguhr and pumice stone. Preference is given to nickel catalysts, particularly in the form of Raney nickel. The catalysts mentioned are added in an amount of 0.1 to 10% by weight, preferably in an amount of 0.5 to 5% by weight, percentages by weight being relative to the weight of the fatty amine used (the percentages by weight mentioned are obviously based on the elements nickel and cobalt, i.e. do not include the support material, for example).

It is advantageous that the starting mixture is substantially free from water. The removal of any water present can be achieved for example by heating the starting mixture (fatty amine and catalyst) to a temperature of above 100° C., preferably to a temperature of 120° to 130° C., and flushing it with nitrogen in a known manner with good stirring. The same is also true of the ammonia content in the starting mixture. Primary fatty amines or fatty amine mixtures originating from the hydrogenation of fatty acid nitriles can contain, as is known, a more or less large amount of ammonia. In this case the primary fatty amine or fatty amine mixture should first be freed from ammonia, as it should be substantially ammonia-free for the hydrogenation according to the invention. Thus the ammonia content should be at most 0.1 mol, preferably at most 0.05 mol, per mole of primary fatty amine used. It is therefore preferred that the primary fatty amine or fatty amine mixture to be hydrogenated by the process according to the invention should be, if not completely, then practically free from ammonia.

The hydrogenation according to the invention is carried out at a pressure (total pressure) of 1 to 40 bar, preferably 1 to 25 bar, and a temperature, depending both on the type and amount of catalyst and the type of primary fatty amine or fatty amine mixture used, in the range from 80° to 160° C., preferably 100° to 140° C. The higher of the stated pressure and temperature values are selected if relatively short reaction times are desired. The supply of hydrogen for hydrogenation into the reaction vessel can be begun before or after heating up to the reaction temperature (it is expedient to add the first quantity of hydrogen before the heating). The hydrogen for hydrogenation can be introduced continuously or in portions, with maintenance of the stated temperature and stated pressure in the reaction vessel, care obviously being taken to ensure intimate contact with the reaction mixture (for example by vigorous stirring, constant pumped circulation or circulation of gas). The hydrogen for hydrogenation is supplied in such a quantity and for such a period that all or substantially all unsaturated bonds are hydrogenated to saturated ones (iodine number determination). If the hydrogenation is carried out at atmospheric pressure, that is without applied pressure, which is likewise possible according to the invention, any entry of air into the reaction vessel should be prevented by appropriate measures. The time for the hydrogenation according to the invention is generally 2 to 6 hours, depending chiefly on the amount of catalyst, the reaction pressure and the reaction temperature.

After completion of the hydrogenation, the desired primary and saturated fatty amine is present. If the separation of the catalyst used and the isolation of a catalyst-free saturated primary fatty amine is desired, this can be achieved for example simply by decanting or filtering. The reaction product can also be subsequently distilled for further purification. The recovered catalyst is also suitable for further hydrogenations according to the invention.

The process according to the invention has a number of advantages. It is simple to carry out. It gives the desired primary saturated fatty amines having an iodine number of less than 5 and in a high yield, that is with negligible quantities of the secondary and tertiary fatty amine by-products. The high yield and purity of the fatty amine are achieved in a relatively short total reaction time. The process according to the invention is thus distinguished by favorable economics. The primary saturated fatty amine obtained is moreover of pale color, and the good color is maintained for example even in the case of alkoxylation reactions. The primary saturated fatty amines in question are known to be valuable products for the preparation of detergents, herbicides, disinfectants, antistatic agents, anticaking agents, textile finishes and flotation agents.

The invention will now be illustrated in greater detail by means of examples.

EXAMPLE 1

700 g (3.5 mol) of primary coconut fatty amine and 30 g of Raney nickel (i.e 4.3% by weight of nickel, relative to the amine), are placed in a 2-l stirred flask. The primary coconut fatty amine has an iodine number of 9 and an ammonia content of 0.04 mol per mole of coconut fatty amine. The hydrogenation of the primary coconut fatty amine is carried out by first flushing the contents of the stirred flask with nitrogen, and then heating them to 140° C. and maintaining them at this temperature. Introduction of hydrogen is begun during the heating, at a rate of 140 l of hydrogen per hour. This supply of hydrogen is continued for 3½ hours. After this time the atmospheric pressure hydrogenation of the double bonds in the carbon chain of the primary coconut fatty amine is completed. A practically saturated primary coconut fatty amine is present, as shown by the iodine number of 3. The yield is 97.0% of theory.

EXAMPLE 2

800 g (3.2 mol) of primary oleylamine having an iodine number of 88 and 40 g of Raney nickel already used three times for the identical reaction (that is 5.0% by weight of nickel, relative to oleylamine) are placed in a 2-l stirred autoclave.

For the hydrogenation of the ammonia-free oleylamine the stirred autoclave is flushed with hydrogen, and hydrogen is then injected to a pressure of 6 bar. After turning on the stirrer and heating the mixture to 135° C., hydrogenation of the double bonds is accomplished by constantly replenishing the consumer hydrogen by means of a pressure regulator and maintaining the cited pressure of 6 bar. After 3½ hours the hydrogenation of the double bonds in the oleyl moiety of the primary oleylamine is completed. The yield of saturated primary amine (stearylamine) is 98.0% of theory. The iodine number of the product is 3.

EXAMPLE 3

35 kg (140 mol) of primary tallow fatty amine and 0.88 kg of Raney nickel already used twice for the identical reaction (i.e. 2.5% by weight of nickel, relative to tallow fatty amine) are introduced into a nitrogen-flushed reactor. The reactor is equipped so that its contents can be pumped into the reactor through a heat exchanger and an injector back. The injector simultaneously draws in gas from the reactor and mixes it intensively with the liquid. The tallow fatty amine has an iodine number of 50 and comprises in detail 65% by weight of primary fatty amine having 18 carbon atoms and 35% by weight of primary fatty amine having essentially 14 and 16 carbon atoms, where 50% by weight is unsaturated primary fatty amine having 1 to 3 double bonds and 50% by weight is saturated primary fatty amine. It contains in addition 0.05 mol ammonia per mole of tallow fatty amine.

For the hydrogenation, the reactor pump is turned on and the reaction mixture is heated up to 130° C. Hydrogen is injected at this temperature up to a pressure of 15 bar, and this pressure, at the temperature mentioned of 130° C., is maintained by constant supply of hydrogen. The hydrogenation of the double bonds is completed after 3 hours. A hardened primary tallow fatty amine is obtained having an iodine number of 4 in a yield of 98.0% of theory.

EXAMPLE 4

35 kg (140 mol) of primary soybean fatty amine and 0.35 kg of Raney nickel (i.e 1.0% by weight of nickel, relative to amine) are introduced into the nitrogen-flushed reactor of Example 3. The soybean fatty amine has an iodine number of 110 and an ammonia content of 0.05 mol per mole of amine and comprises in detail 15% by weight of $C_{16}$-alkylamine, 80% by weight of $C_{18}$-alkylamine and 5% by weight of $C_{14}$-, $C_{20}$- and $C_{22}$-alkylamine, where 75% by weight of the $C_{18}$-alkylamine contain 1, 2 or 3 double bonds.

For the hydrogenation, the reactor pump is turned on and the reaction mixture is heated up to 105° C. and maintained at this temperature. During the heating hydrogen is injected to a pressure of 25 bar, and this hydrogen pressure is maintained until no further fall in pressure is detectable, which is the case after 5½ hours. A hardened primary soybean fatty amine having an iodine number of 2 is obtained in a yield of 97.0% of theory.

We claim:

1. A process for the preparation of saturated primary fatty amines by hydrogenation of unsaturated primary fatty amines in liquid phase in the presence of nickel catalysts or cobalt catalysts, which comprises reacting the unsaturated primary fatty amine with hydrogen in the presence of 0.1 to 10% by weight of the catalyst, relative to the fatty amine, at a temperature of 80° to 140° C. and a pressure of 1 to 40 bar.

2. The process as claimed in claim 1, in which the unsaturated primary fatty amine is reacted with hydrogen in the presence of 0.5 to 5% by weight of the catalyst, relative to the fatty amine, at a temperature of 100° to 140° C. and a pressure of 1 to 25 bar.

3. The process as claimed in claim 1, in which nickel catalysts are used.

4. A process as claimed in claim 1, wherein said unsaturated fatty amines have 8 to 22 carbon atoms.

5. A process as claimed in claim 1, wherein said unsaturated fatty amines have 12 to 18 carbon atoms.

6. A process as claimed in claim 1, wherein said unsaturated primary fatty amine is substantially free from water.

7. A process as claimed in claim 1, wherein said unsaturated primary fatty amine is heated to a temperature above 100° C.

8. A process as claimed in claim 1, wherein said unsaturated primary fatty amine is heated to a temperature of 120° to 130° C.

9. A process as claimed in claim 1, wherein said unsaturated primary fatty amine is primary coconut fatty amine.

10. A process as claimed in claim 1, wherein said unsaturated primary fatty amine is primary tallow fatty amine.

11. A process as claimed in claim 1, wherein said unsaturated primary fatty amine is primary soybean fatty amine.

12. A process as claimed in claim 1, wherein said unsaturated primary fatty amine is primary oleylamine.

* * * * *